(12) United States Patent
da Cunha (10) Patent No.: US 7,053,522 B1
(45) Date of Patent: May 30, 2006

(54) SURFACE ACOUSTIC WAVE SENSOR

(75) Inventor: Mauricio Pereira da Cunha, Orono, ME (US)

(73) Assignee: University of Maine System Board of Trustees, Bangor, ME (US)

( * ) Notice: Subject to any disclaimer, the term of this patent is extended or adjusted under 35 U.S.C. 154(b) by 334 days.

(21) Appl. No.: 10/374,403

(22) Filed: Feb. 26, 2003

(51) Int. Cl.
*H01L 41/08* (2006.01)

(52) U.S. Cl. .................................. 310/313 A
(58) Field of Classification Search ............. 310/313 R, 310/313 A, 313 B, 360
See application file for complete search history.

(56) References Cited

U.S. PATENT DOCUMENTS

| | | | |
|---|---|---|---|
| 5,686,779 A | 11/1997 | Vig | |
| 5,744,902 A | 4/1998 | Vig | |
| 5,821,673 A | 10/1998 | Pisarevsky et al. | |
| 5,905,325 A | * 5/1999 | Naumenko et al. | 310/313 A |
| 5,917,265 A | 6/1999 | Naumenko et al. | |
| 6,005,325 A | 12/1999 | Inoue et al. | |
| 6,031,315 A | 2/2000 | Abbott | |
| 6,054,794 A | * 4/2000 | Naumenko et al. | 310/313 A |
| 6,084,333 A | * 7/2000 | Inoue et al. | 310/313 A |
| 6,097,131 A | 8/2000 | Naumenko et al. | |
| 6,186,005 B1 | 2/2001 | Leidl | |
| 6,317,014 B1 | * 11/2001 | Kadota | 333/133 |
| 6,323,577 B1 | * 11/2001 | Inoue et al. | 310/313 A |
| 6,370,955 B1 | 4/2002 | Tuller et al. | |

OTHER PUBLICATIONS

I.B. Yakovkin et al., Numerical and Experimental Investigation SAW in Lagasite, 1995 IEEE Ultrasonics Symposium, pp. 389–392.

V. P. Plessky et al., Surface Transverse Waves on Langasite, 1998 IEEE Ultrasonics Symposium, pp. 139–142.

H. J. Whitehouse et al., High Temperature Ultrasonic Devices for Harsh Environments (Abstract), 2000 IEEE Ultrasonics Symposium.

Pereira da Cuna et al., Experimental and Predicted SAW Temperature Behavior of Langatate, 2000 IEEE Ultrasonics Symposium, pp. 245–248.

Pereira da Cuna et al., Pure Shear Horizontal SAW on Langatate, 2000 IEEE Ultrasonics Symposium, pp. 231–234.

Pereira da Cuna et al., LGX Pure Shear Horizontal SAW for Liquid Sensor Applications, Proceedings of the 2002 IEEE Sensors, Jun. 2002.

Pereira da Cuna et al., Surface and Pseudo Surface Acoustic Waves in Langatate: Predictions and Measurements, 2002 IEEE Trans. Ultrason. Ferroecec. Freq. Contr., Sep. 2002, pp. 1291–1299.

Pereira da Cuna et al., High Coupling, Zero TCD SH Wave on LGX, 2002 IEEE Ultrasonics Symposium, Oct. 2002.

* cited by examiner

*Primary Examiner*—Mark Budd
(74) *Attorney, Agent, or Firm*—MacMillan, Sobanski & Todd, LLC (57) ABSTRACT

A Surface Acoustic Wave (SAW) Device that includes a substrate formed from a material selected from the LGX family of crystals and having a SAW propagation surface defined by Euler angles relative to the corresponding crystal axes having a range of $-5°<\phi<+5°$, $-5°<\theta<50°$ and $80°<\psi<100°$. The device being utilized for liquid sensor applications including the detection of chemical or biological agents present in a liquid environment. The device may or may not include the deposition of one or more chemical and/or biological films upon the propagation surface to enhance the sensitivity thereof. At least one interdigital transducer is formed upon the substrate propagation surface and that is operative to launch surface acoustic waves having a shear horizontal mode.

36 Claims, 8 Drawing Sheets

SURFACE ACOUSTIC WAVE SENSOR

BACKGROUND OF INVENTION

This invention relates in general to surface acoustic wave sensors and in particular to a surface acoustic wave sensor for a liquid sensor application that utilizes a shear horizontal or quasi shear horizontal mode of wave propagation along a predetermined axis.

Surface Acoustic Wave (SAW) devices are electronic components that generate guided acoustic waves along a surface of the device. SAW devices are generally fabricated on single crystal anisotropic substrates that are also piezoelectric. SAW devices typically include one or more pairs of intertwined interdigital electrodes that form transducers to convert the electrical signals applied to the device into the electromechanical surface acoustic waves generated in the device. The devices also may have one or more thin film layers deposited upon the substrate surface.

SAW sensors are among the most sensitive and widely used physical and chemical sensors in gas and liquid environments because the propagating acoustic wave has its energy concentrated close to the device surface. Along an arbitrary surface wave propagation direction, a particle in the substrate material describes an elliptical trajectory, with displacement components normal and parallel to the device surface. For a liquid sensor application, any SAW device operational mode with a significant particle displacement component normal to the surface suffers severe attenuation, thus compromising the device performance. Accordingly, for a liquid sensor, it is desirable that the selected operational mode presents a high or exclusive particle displacement component parallel to the substrate surface, since this acoustic mode is less attenuated by the presence of the liquid than in the case of particle displacement that is normal to the substrate surface.

A SAW that satisfies the above described particle displacement condition is the Shear Horizontal (SH) wave, also known as a Surface Transverse Wave (STW). Pure, piezoelectrically active, SH waves occur along propagation directions in which the sagittal purely mechanical displacement components are uncoupled from the electrical fields of the device and the shear horizontal displacement components of the waves, leading to two separate solutions along those propagation directions. One solution is a purely mechanical sagittal SAW while the other solution is a stiffened shear horizontal wave mode that is generated by the interdigital transducers described above. Both SAW solutions can exist on rotated Y cuts of trigonal class 32 crystals.

One trigonal class 32 crystal is quartz. However, with respect to SAW devices to be utilized as liquid sensors, use of SH-SAW on quartz crystals for liquid sensing applications poses a problem in that the effective permittivity of quartz is around 4.6, and thus the interdigital transducers are electrically shorted by the presence of high relative permittivity fluids, such as water, which has a relative permittivity around 80.

The trigonal class 32 crystals also includes the LGX family of crystals, which comprise langatate (LGT, $La_3Ga_{5.5}Ta_{0.5}O_{14}$), langasite (LGS, $La_3Ga_5SiO_{14}$), langanite (LGN, $La_3Ga_{5.5}Nb_{0.5}O_{14}$), and variations, such as LGTS $La_3Ga_{5.25}Ta_{0.25}Si_{0.5}O_{14}$) and LGZS ($La_3Ga_5Zr_{0.5}Si_{0.5}O_{14}$). While the LGX family of crystals can also present SH-SAW, for liquid sensing applications, theoretical predictions and experimental verification for crystals of the LGX family along known propagation directions defined by Euler angles (0°, 70°, 90°) and (0°, 132°, 90°), have shown that these orientations have a high penetration depth inside the surface. The high penetration depth translates into a weakly surface guided wave, with the wave energy penetrating significantly inside the substrate. Accordingly, the sensitivity to any surface perturbation, a necessary mechanism for a liquid sensor application, is reduced for known sensors using the LGX family of crystals along the orientations with the above Euler angles.

A Pseudo Surface Acoustic Wave (PSAW) is another known type of acoustic wave mode that has been used for liquid sensing, in particular along 36° Y rotated X propagation with a substrate formed from LiTaO3 material, which is referred to as a 36° Y SAW device in the following descriptions. However, disadvantages of this mode with respect to the SH-SAW are the fact that the PSAW is not strictly guided, and therefore a spurious Bulk Acoustic Wave (BAW) is generated in the device, increasing the losses, and ultimately degrading the performance.

Accordingly, it would be desirable to provide a SH-SAW sensor that could be utilized as a liquid sensor.

SUMMARY OF INVENTION

This invention relates to a surface acoustic wave sensor for a liquid sensor application that utilizes a shear horizontal or quasi shear horizontal mode of wave propagation along a predetermined axis.

It is the object of the present invention to provide an LGX family of crystals having an orientation range defined by the first, second, and third Euler angles (phi, theta, psi, also known by ($\phi$, $\theta$, and $\psi$), such that a Shear Horizontal Surface Acoustic Wave (SH-SAW) or a Quasi-Shear Horizontal Surface Acoustic Wave (QSH-SAW) is supported and applicable to the development of liquid sensors. In particular, the inventor has determined that a specified crystal orientation with $-5°<\phi<+5°$, $-5°<\theta<50°$ and $80°<\psi<100°$ provides a superior SH-SAW liquid sensor. At least one interdigital transducer is formed upon the surface of the sensor. The inventor also has determined that the SH-SAW along the specified orientations have an electromechanical coupling about one order of magnitude stronger than a prior art 36° Y rotated quartz SH orientation, zero Temperature Coefficient of Delay (TCD), and zero Power Flow Angle (PFA). Additionally, the phase velocities for the SH-SAW and QSH-SAW operational modes of a device in accordance with the invention are approximately 55% below the phase velocity of the known SAW device with the 36° Y rotated quartz, and the wave energy concentrated within seven wavelengths, about eight times shallower than the penetration depth for the 36° Y rotated quartz device, and about 17 times shallower than the penetration depth of a prior art LGT device having Euler angles (0°, 132°, 90).

It also is an object of the invention to provide a method for forming a Surface Acoustic Wave (SAW) Device that includes a single crystal selected from one of the group of langatate (LGT, $La_3Ga_{5.5}Ta_{0.5}O_{14}$), langasite (LGS, $La_3Ga_5SiO_{14}$), langanite (LGN, $La_3Ga_{5.5}Nb_{0.5}O_{14}$), and variations, such as LGTS ($La_3$ $Ga_{5.25}Ta_{0.25}Si_{0.5}O_{14}$) and LGZS ($La_3Ga_5Zr_{0.5}Si_{0.5}O_{14}$. The crystal is oriented for cutting a planar surface with the crystal orientation defined by the Euler angles having a range of $-5°<\phi<+5°$, $-5°<\theta<50°$ and $80°<\psi<100°$. The crystal is then cut to form the planar surface with the cut defined by the above ranges for the Euler angles. At least one thin film interdigital transducer is formed upon the substrate propagation surface, the transducer being operative to generate surface acoustic waves propagating in a direction along an axis of propagation defined relative to the crystal Euler angles ($\phi$, $\theta$, $\psi$).

Various objects and advantages of this invention will become apparent to those skilled in the art from the following detailed description of the preferred embodiment, when read in light of the accompanying drawings.

DETAILED DESCRIPTION

Figure 1:
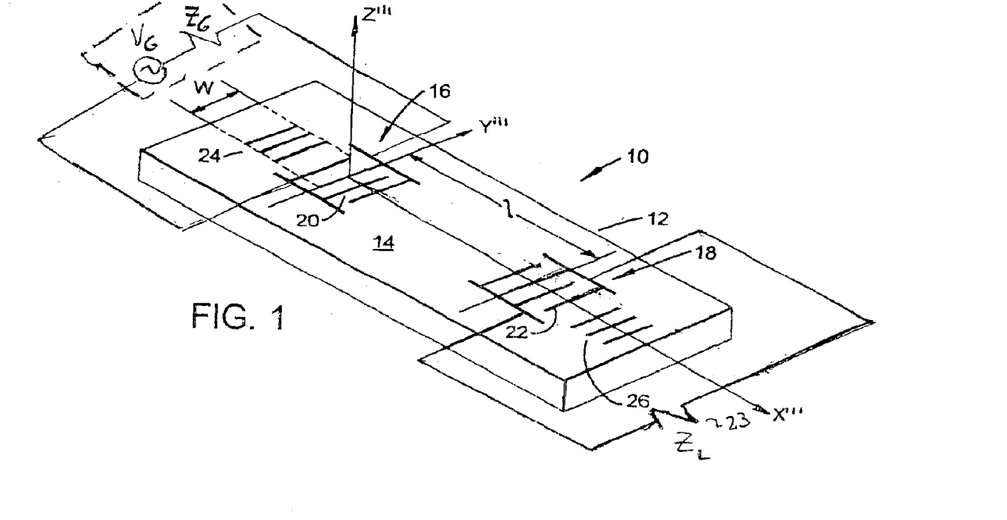
FIG. 1 is a perspective view of a Surface Acoustic Wave delay line device in accordance with the invention.

Referring again to the drawings, there is illustrated in FIG. 1, a SAW device 10 for a liquid sensor application that is in accordance with the invention. The device 10 includes a substrate 12 formed from a crystal selected from the LGX family of crystals. As described above, the LGX family of crystals are materials of the trigonal crystal class 32, which is the same crystal class as quartz. The LGX family of crystals includes langatate (LGT, $La_3Ga_{5.5}Ta_{0.5}O_{14}$), langasite (LGS, $La_3Ga_5SiO_{14}$), langanite (LGN, $La_3Ga_{5.5}Nb_{0.5}O_{14}$), and variations, such as LGTS ($La_3Ga_{5.25}Ta_{0.25}Si_{0.5}O_{14}$) and LGZS ($La_3Ga_5Zr_{0.5}Si_{0.5}O_{14}$).

In FIG. 1, an input Interdigital Transducer (IDT) 16 is fabricated upon the upper surface 14 of the substrate 12, such as, for example, by conventional thin film deposition methods and photolithography utilizing ultra-violet light. The IDT 16 includes interdigital electrodes having a plurality of intertwined fingers 20. The input transducer 16 is of conventional design and is connected to an electrical signal generator 21. The input transducer 16 is responsive to excitation by the generator 21 to generate surface acoustic waves that propagate across the upper surface 14 of the substrate 12. The surface acoustic waves propagate along the axis labeled X''' and are received by an output Interdigital Transducer (IDT) 18 that also is formed upon the upper surface 14 of the substrate 12 by conventional thin film technology. Similar to the input IDT 16, the output IDT 18 includes interdigital electrodes having a plurality of intertwined fingers 22. The output IDT 18 is operative to convert the electromechanical surface acoustic waves into an electrical signal that is applied to an electrical load labeled 23.

As also shown in FIG. 1, reflecting electrodes 24 and 26 are formed upon the ends of the substrate upper surface 14; however, these electrodes are optional. Additionally, one or more chemical and/or biological films (not shown) can be optionally deposited on the upper surface 14 of the substrate 12 to enhance detection of chemical or biological agents present in the liquid environment.

Figure 2:
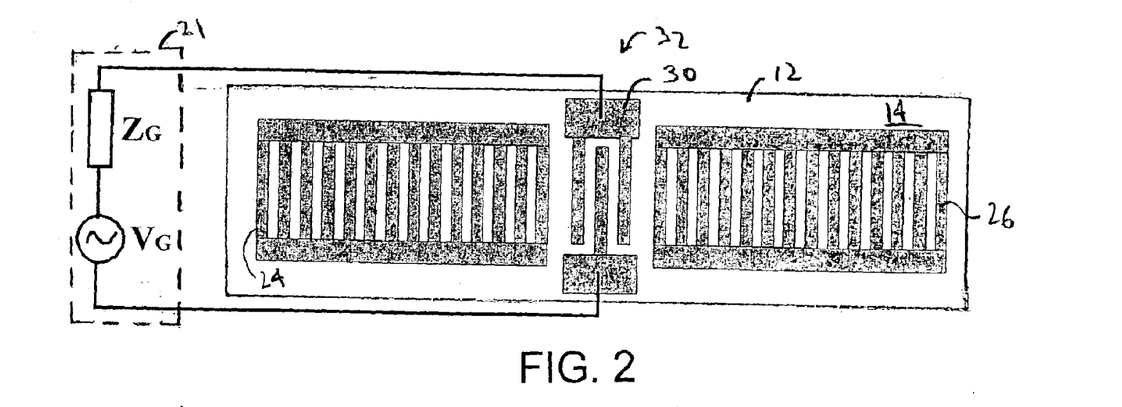
FIG. 2 is a planar view of a Surface Acoustic Wave one port resonator device in accordance with the invention.
Figure 3:
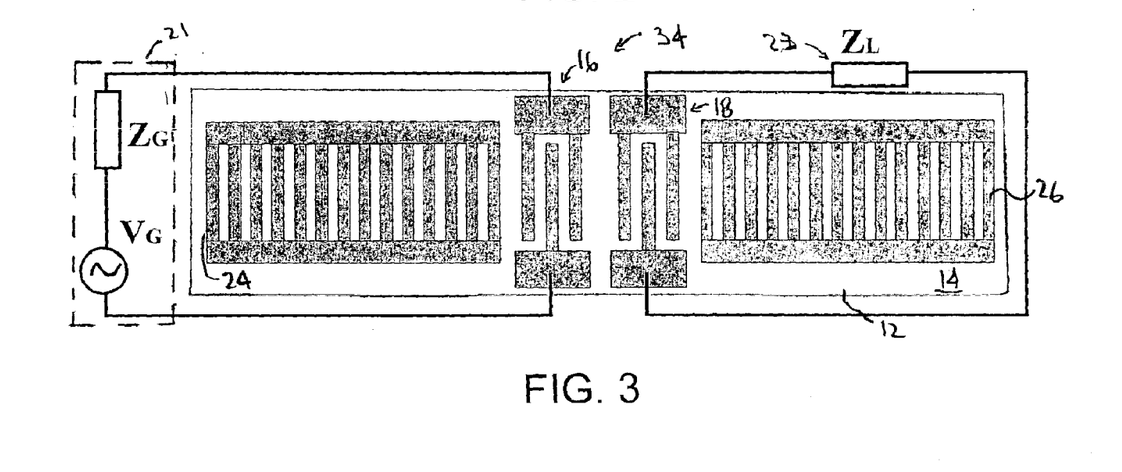
FIG. 3 is a planar view of a Surface Acoustic Wave two port resonator device in accordance with the invention.

While the preferred configuration of the SAW device 10 is illustrated in FIG. 1 as a delay line, it will be appreciated that the device 10 also can be configured as a single port transducer structure 30 with a resonator type of structure 32, as shown in FIG. 2. Alternately, the device 10 also can be configured with input and output transducers in a two-port resonator type of structure 34, as shown in FIG. 3. The invention also can be practiced with other variations of IDT configurations that are applicable for the liquid sensors (not shown). Components shown in FIGS. 2 and 3 that are similar to components shown in FIG. 1 have the same numerical designators.

Figure 4:
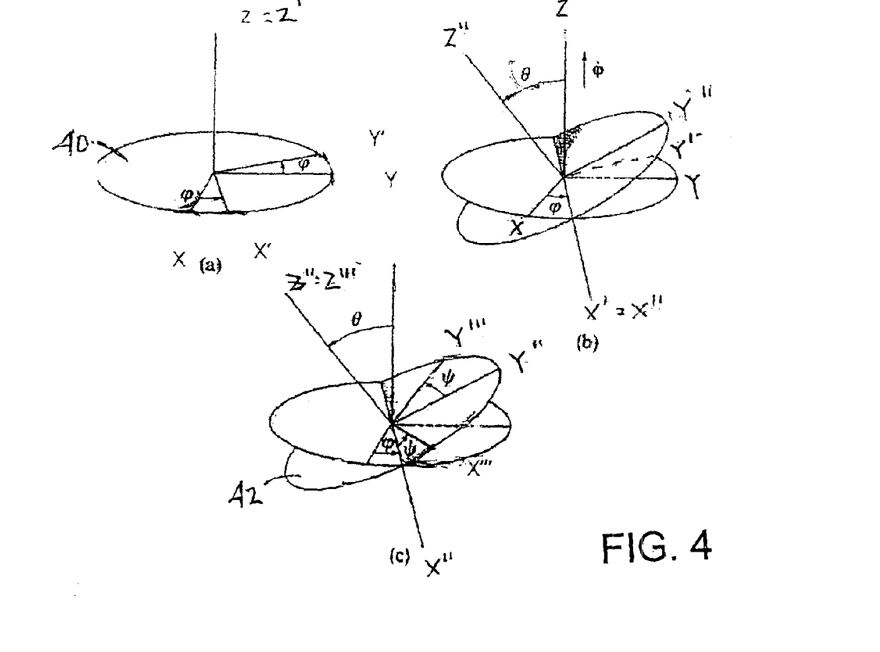
FIG. 4 illustrates the Euler angles that describe the orientation of the rotated substrate crystal axes of the device shown in FIG. 1 and the direction of SAW propagation on the device with respect to the unrotated crystalline axes.

As illustrated in FIG. 4, the uncut LGX material is referenced by three orthogonal axes labeled X, Y and Z, while the surface 14 of the cut LGX material forming the SAW device substrate 12 is referenced by three orthogonal axes labeled X''', Y''' and Z'''. The elliptical surface labeled 40 in FIG. 4 represents the orientation of the crystals within the uncut LGX material, while the tipped elliptical surface labeled 42 represents the orientation of the crystals within the cut LGX material forming the substrate 12. Thus, the tipped surface 42 has the same spatial orientation as the upper surface 14 of the SAW device substrate 12. Therefore, the tipped surface 42 will be referred to as the surface 14 in the following description.

The spatial relationship between the two surfaces 40 and 14 are defined by first, second and third Euler angles, designated $\phi$, $\theta$ and $\psi$, respectively. The Euler angles represent rotations about the axes of the LGX material 40, to orient the axes, X''', Y''' and Z''', of the cut crystal surface 14. According to convention, the cut surface 14 is considered as being rotated first about the Z axis to offset the X' axis from the X axis by the first Euler angle φ, as illustrated in FIG. 4(a). In FIG. 4(a) the other two axes are designated Y' and Z' following the first rotation. A second rotation then occurs about the X' axis by the second Euler angle θ to offset the Z'' axis from the Z', as illustrated in FIG. 4(b). In FIG. 4(b), the other two axes are designated X'' and Y'' following the second rotation. Finally, the crystal is rotated about the Z'' axis to offset the X''' axis from the X'' axis by the third Euler angle ψ, as shown in FIG. 4(c). In FIG. 4(c), the other two axes are designated Y''' and Z''' following the third rotation. Thus, the surface 14 of the cut LGX crystals is perpendicular to rotated axis Z''' and the electrodes 20 and 22 of the IDTs 16 and 18, respectively, are perpendicular to axis X''' and parallel to axis Y'''.

Use of the Euler angles (φ, θ, ψ) defines a unique substrate orientation. The inventor has determined that a particular Quasi-Shear Horizontal SAW (QSH-SAW) can be generated upon a crystal selected from the LGX family that is cut to have an orientation that falls within specific ranges of the Euler angles that is appropriate for liquid sensing applications and comprises the preferred embodiment of the object of this invention. The quasi-shear horizontal SAW is generated by a SAW device having a LGX crystal cut to provide a crystal orientation defined by the Euler angle φ being within a range from −5° to 5°; the Euler angle θ, within a range from −5° to 50°; and the Euler angle ψ, within a range from 80° to 100°. As the ranges of the Euler angles is narrowed, the QSH-SAW approaches a pure SH-SAW. However, the QSH-SAW that exists for the above ranges already provides a significant enhancement of sensor performance for liquid measurement applications.

Several significant and unexpected improvements are obtained with the present invention. These improvements include concentration of the wave energy near the surface of the SAW device. The energy of the SH mode for the LGX orientations specified are concentrated within seven wavelengths, about eight times shallower than the penetration depth for the prior art 36° Y rotated quartz device described above. The present invention also operates with a SH-SAW penetration depth that is about 17 times shallower than the penetration depth of a known LGT SAW device having Euler angles defined by (0°, 132°, 90). The later know device was previously reported by the inventor in the IEEE 2000 International Ultrasonic Symposium Proceedings.

Figure 5:
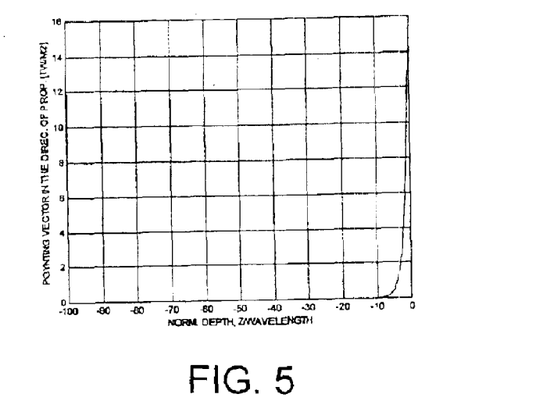
FIG. 5 is a plot of the Poynting vector in the direction of propagation versus the normalized depth inside the substrate for propagation along the SH-SAW LGT Euler angles (0°, 13.5°, 90°) for the SAW device shown in FIG. 1.
Figure 6:
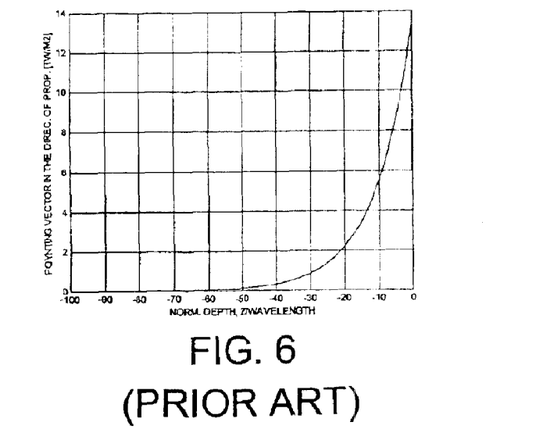
FIG. 6 is a plot of the Poynting vector in the direction of propagation versus the normalized depth inside the substrate for propagation along the SH-SAW on quartz Euler angles (0°, 54.2°, 90°) for a prior art SAW device.
Figure 7:
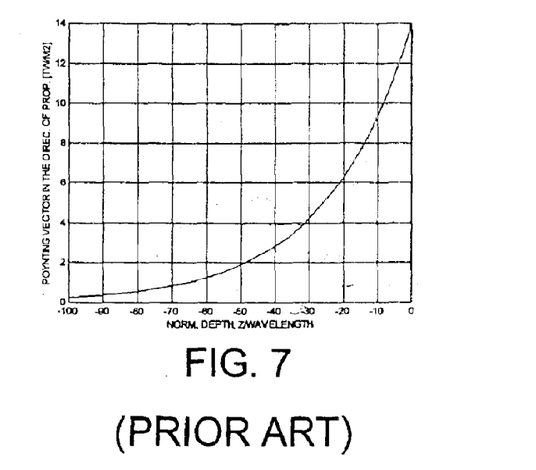
FIG. 7 is a plot of the Poynting vector in the direction of propagation versus the normalized depth inside the substrate for propagation along the SH-SAW on LGT Euler angles of (0°, 132°, 90°) for another prior art SAW device.

As an exemplification of this property, FIG. 5 shows a plot of the Poynting vector in the direction of propagation versus the normalized depth inside the substrate for a typical LGX substrate and orientation with the Euler angles within the ranges specified above for the invention. Specifically, the substrate material and Euler angles for the SAW device shown in FIG. 5 are LGT and (0°, 13.5°, 90°), respectively. A similar plot of the Poynting vector for a known 36° Y quartz SAW device having Euler angles of (0°, 54.2°, 90°) is shown in FIG. 6 for comparison. Upon comparing FIG. 5 to FIG. 6, it is seen that the energy is clearly concentrated within about seven wavelengths of the surface of the SAW device 10 that is in accordance with the present invention, while the energy approaches a depth of about 60 wavelengths of the surface of the quartz prior art device shown in FIG. 6. To further illustrate the invention, another similar plot of the Poynting vector for a known LGT device having Euler angles of (0°, 132°, 90°) is shown in FIG. 7. A comparison of FIG. 7 to FIG. 5 shows that a LGT device that is in accordance with the invention concentrates the wave energy 17 times more that the prior art LGT device shown in FIG. 7.

With prior art devices, deep penetration of the SAW into the substrate of prior art devices causes excitation of plate modes and reflections from the back substrate surface, as has been observed and discussed in the above referenced IEEE Symposium Proceeding. However, for the present invention, the inventor has found that the concentration of SAW energy close to the substrate surface significantly reduces the excitation of plate modes and reflections from the substrate back surface. In addition, the shallow penetration depth along this propagation direction is attractive for liquid sensor applications since it increases the device sensitiveness. Also, these modes are strictly guided, thus avoiding inherent spurious bulk generation, as observed for pseudo modes, such as occur in the prior art 36° YX LiTaO₃ propagation direction.

The present invention also provides a higher electromechanical coupling, $K^2$, than prior art devices. The electromechanical coupling is defined by the following formula:

$$K^2 = 2|v_{pf} - v_{pm}|/v_{pf}, \text{ where}$$

$v_{pf}$=phase velocity for free surface and $v_{pm}$=phase velocity for metallized surface.

Figure 8:
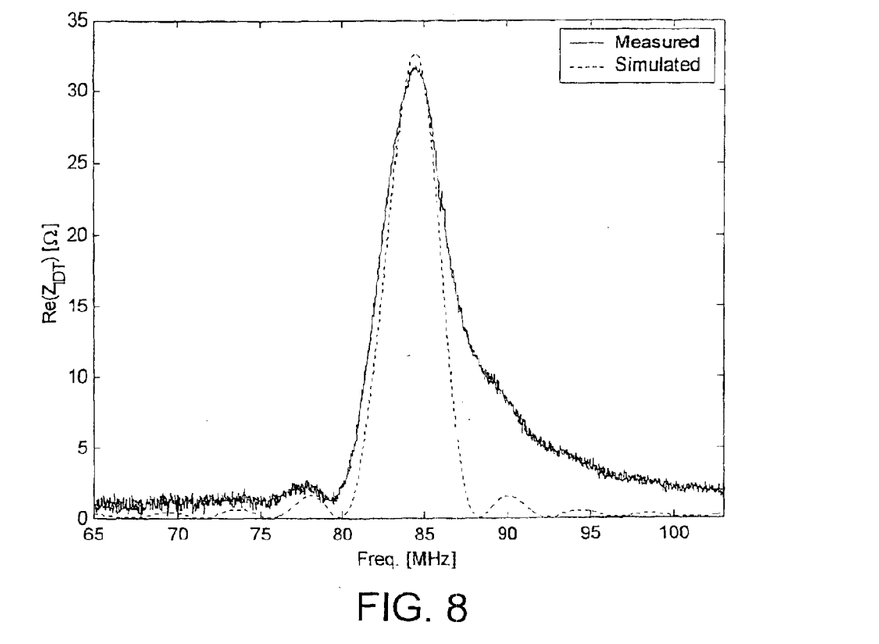
FIG. 8 is a plot of the measured and simulated real part of the IDT input impedance along a typical SH-SAW LGX propagation direction for an interdigital transducer included in the SAW devices shown in FIGS. 1 through 3.

Measured and simulated fitting for the IDT input impedance have been performed for a SAW device in accordance with the invention that has an LGX substrate and the Euler angles previously specified for the present invention. The IDT input impedance determined for the device that is in accordance with the invention correlates to an electromechanical coupling of around $K^2=0.8\%$. This electromechanical coupling value is about 10 times higher than the coupling of an equivalent prior art 36° Y quartz SAW device. FIG. 8 shows the measurement of the real part of the IDT input impedance from which the electromechanical coupling was extracted for the SAW device in accordance with the invention and formed from LGT material with Euler angles defined by (0°, 13.5°, 90°) to exemplify this property. The solid line in FIG. 8 represents the actual measurement of the impedance while the dashed line represents the result obtained from a simulation of the device that is in accordance with the invention. The SH-SAW device used to extract the effective electromechanical coupling included an IDT structure comprising a split finger configuration having 80 fingers of 4 μm width and a mark to space ratio of 1:1. The input and output IDT's 16 and 18 were separated by 30λ. The metallic films deposited upon the surface 14 of the SAW device substrate 12 consisted of 1300 Å layer of Al on top of a 100 Å adhesion layer of Cr.

Figure 9:
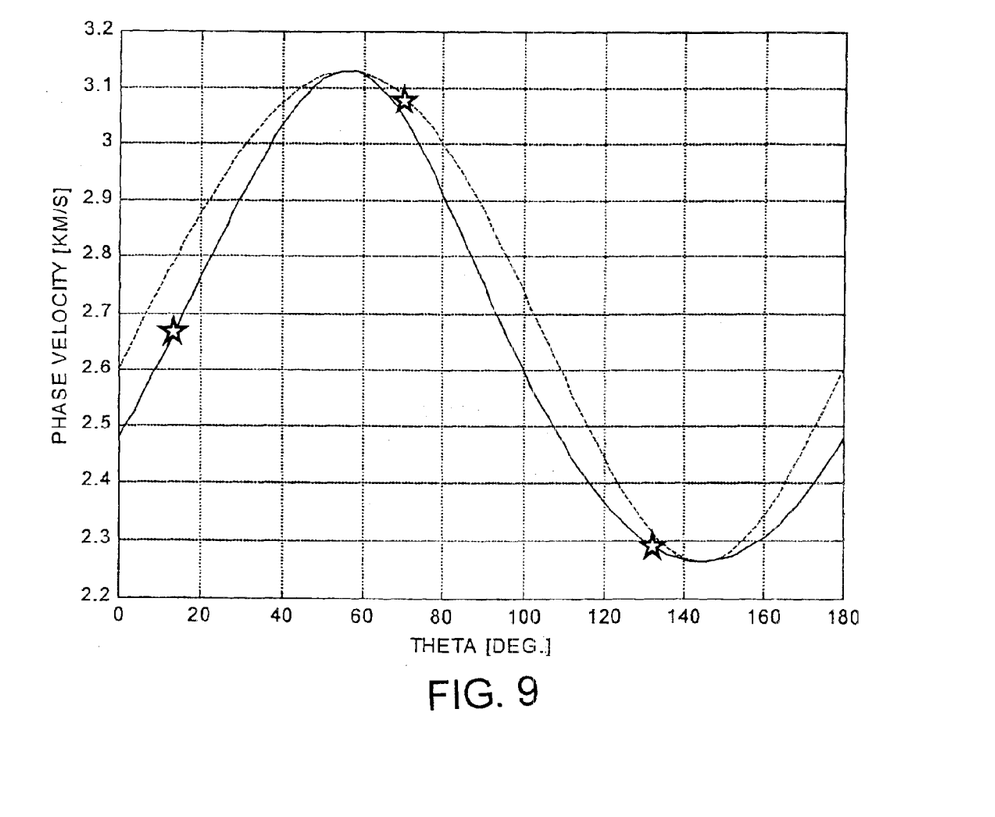
FIG. 9 is a plot of measured and simulated SH-SAW phase velocities for the SAW device shown in FIG. 1.

Additionally, the phase velocity for the surface waves with the present invention is reduced from the phase velocities for prior art SAW devices. The phase velocities for SAW devices having LXG substrates and crystal orientations within the Euler angles previously specified are around 2650 m/s. This velocity is about 55% below the phase velocity of prior art 36° Y quartz SAW devices, thus leading to smaller Surface Transverse Wave (STW) devices. Predicted and measured values for the phase velocity for LGT SAW devices with Euler angles defined by LGT (0°, θ, 90°), that are in accordance with the present invention, are shown in FIG. 9, where the solid line represents the predicted SH values and the stars represent measured values. The dashed line in FIG. 9 represents a pure shear polarized Bulk Acoustic Wave (BAW) that is included in the figure for reference. In the case of θ=13.5°, which lies within the second Euler angle range specified for the invention, the measured phase velocity is 2660 m/s, which is within 0.2% of the calculated value.

The metal strip reflectivity for the LXG substrates and orientations within the Euler angles previously specified has been predicted and measured by the inventor to be around $10^{-3}$ for an aluminum metal strip of thickness h normalized to the wavelength, λ, with a h/λ of around 1%. This reflectivity value is appropriate to design reflective based devices, such as the devices illustrated in FIGS. 2 and 3. Moreover, the thickness of the aluminum reflector can be increased to values up to h/λ≈120% and other film materials, such as Gold or Platinum, can be used to increase the reflectivity if required.

Figure 10:
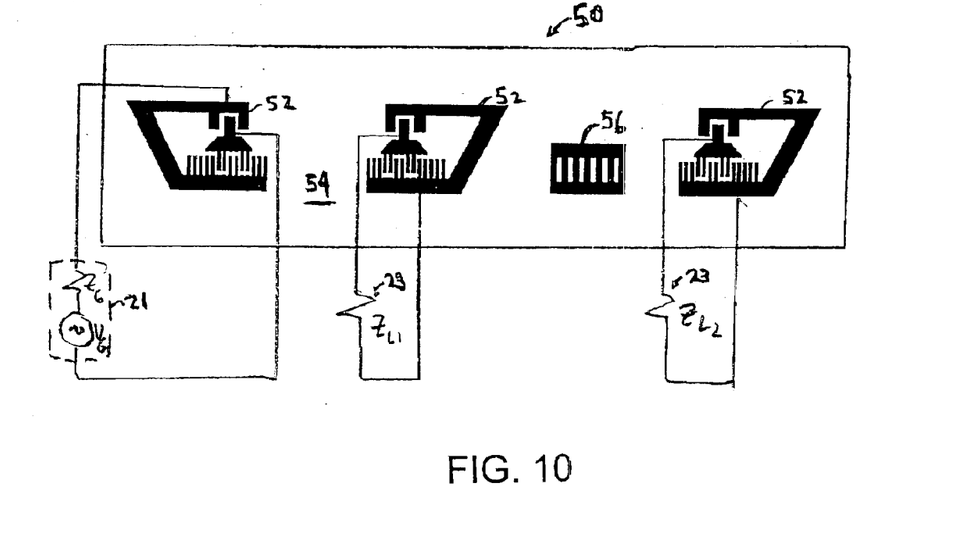
FIG. 10 is a plan view of an alternate embodiment of the SAW device shown in FIG. 1 that is utilized to measure electrode reflectivity.

A device 50 used to extract the above electrode reflectivity data is show in FIG. 10. Components shown in FIG. 10 that are similar to components shown in FIG. 1 have the same numerical designators. The device 50 has a plurality of IDT's 52 deposited upon the surface of a substrate 54 formed from LGT material with Euler angles of (0°, 13.5°, 90°). Each of the IDT's 52 shown in FIG. 9 has 80 fingers, two electrodes per λ, 50λ aperture, finger width 5 μm and mark to space ratio of 1:1. A short-circuited reflector 56 also is deposited upon the substrate surface and has 80 electrodes. A metallic film is deposited upon the substrate 54 and consists of a 1300 Å layer of Al on top of a 100 Å adhesion layer of Cr.

Figure 11:
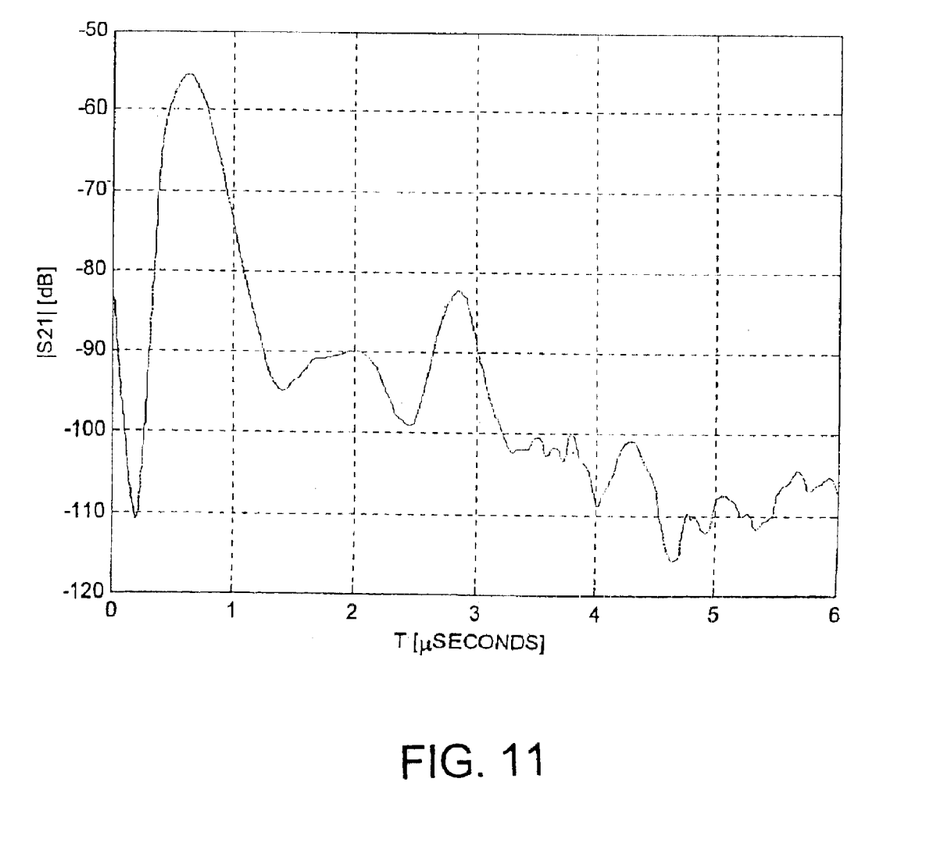
FIG. 11 illustrates the Fast Fourier Transform of data measured with the SAW device shown in FIG. 10.

FIG. 11 illustrates a Fast Fourier Transform for the scattering parameter $S_{21}$, data measured for the device structure shown in FIG. 9. The main peak around 630 ns is the transmission signal between two device IDTs. The second peak around 1.9 μs is the triple transit response, and the third peak around 2.9 μs is the reflected signal from the short-circuited grating. Some electromagnetic feed-through can also be observed close to the time origin. An aluminum strip reflectivity of around $10^{-3}$ has been obtained for the shorted grating measured.

The LGX family of crystals with orientations within the Euler angles previously specified for the present invention have values of relative dielectric permittivity around 38, more than eight times the values of relative dielectric permittivity observed in quartz. The prior art SH-SAW device with 36° Y quartz suffers severe attenuation by water, since the effective permittivity of the quartz is about 4.5. Thus, the IDT's are electrically shorted by the presence of water that has a relative permittivity around 80.

The higher relative dielectric permittivity of the present invention SAW device prevents the electrical field lines from strongly diverging from the piezoelectric material into the liquid environment, which would null the IDT structures excitation of the electro mechanical wave in the piezoelectric substrate. This fact and the shear polarization of the SH wave explain the reduced attenuation of the SH-SAW and QSH-SAW in LGX under water loading conditions along the propagation directions for the present invention. This reduced attenuation, due to the higher relative permittivity compared to quartz, has been experimentally verified and is discussed in the next section.

Experimental Results

A delay line, such as the one schematically rep resented in FIG. 1 and resonator structures such as the ones schematically represented in FIGS. 2 and 3, respectively have been designed, fabricated, and tested. The fabricated delay line consisted of two identical split fingers IDT's having 50λ aperture; 160 fingers of 4 μm width and mark to space ratio of 1:1, and 95 λ center-to-center distance. The fabricated resonator structures included both one and two-port devices, with either one or two IDT's, respectively, formed mostly from aluminum. Each of the resonator IDT's has 80 fingers, a 50 wavelength (λ) aperture, 500 strip short circuit reflectors, 4 μm finger width and mark to space ratio of 1:1. Both of the delay line and the resonator structures included a metallic film deposited upon the substrate that consisted of 1300 Å metal layer of Aluminum (Al) on top of a 100 Å adhesion layer of Chromium (Cr). However, it will also be appreciated that metallic film can include Gold (Au) or Platinum (Pt) for the metal layer and that the adhesive layer can include Titanium (Ti) or Nickel Chromium (NiCr). Additionally, for the metal layer, the Al can have a thickness within a range of 400 Å to 5,000 Å, the Au can have a thickness within a range of 400 Å to 3,000 Å and the Pt can have a thickness within a range of 400 Å to 2,000 Å. Both of the delay line and the resonator structures were fabricated along LGT Euler angles (0°, 13.5°, 90°) to verify the following described properties.

Figure 12:
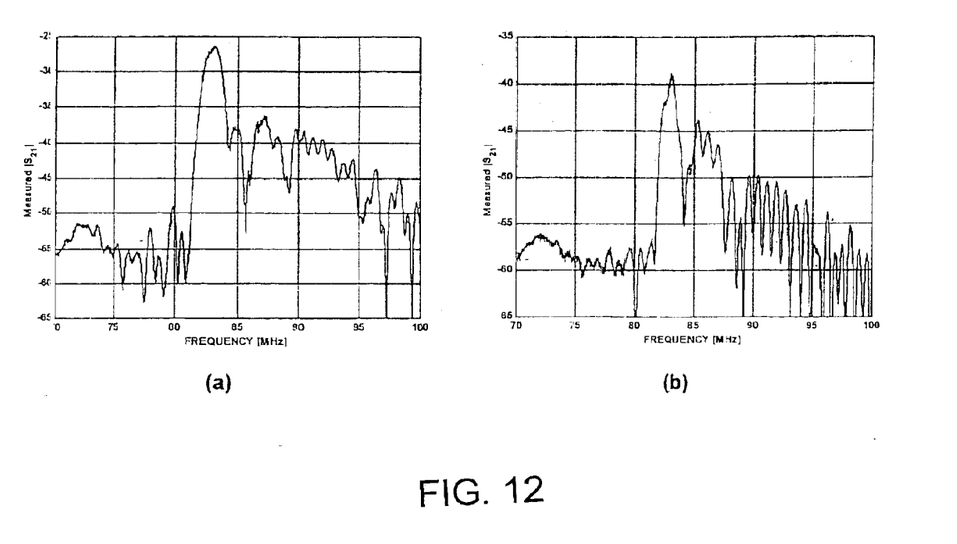
FIGS. 12a and 12b illustrate the behavior of the SAW delay line device structure shown in FIG. 1 under unloaded surface and De-Ionized water loaded surface conditions, respectively.
Figure 13:
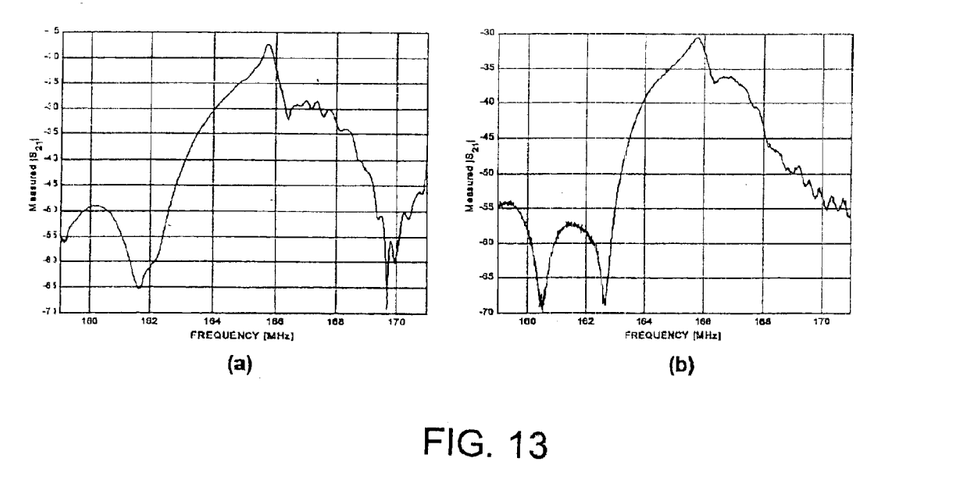
FIGS. 13a and 13b illustrate the behavior of the SAW resonator device structure shown in FIG. 3 under unloaded surface and De-Ionized water loaded surface conditions, respectively.

FIGS. 12 and 13 show the behavior of the fabricated delay line and the two port resonator structures, respectively, that were described in the previous paragraph. The surface condition of no liquid loading on the SAW devices surface is shown in FIGS. 12a and 13a, while the surface condition of a liquid loading with De-Ionized (DI) water is shown in FIGS. 12b and 13b. In both cases, the attenuation with the addition of the DI water is around 13 dB, a moderate attenuation for water loading. A similar experiment with the same delay line and resonator structures on a quartz ST-X device resulted in signal attenuation in excess of 40 dB. The severe attenuation for ST-X quartz has two major causes. First, ST-X quartz has a generalized SAW propagation direction, with a strong normal to the surface polarization component, which is severely attenuated by the water. Secondly, the effective permittivity of ST-X quartz is about 4.6, and thus the IDT's are electrically shorted by the presence of the DI water that has a relative permittivity around 80.

FIGS. 12 and 13 also illustrate the presence of plate modes and reflections from the back of the LGX wafer. These modes can be significantly reduced by sandblasting the back surface of the substrate, as previously verified by the inventor.

In addition to the experiment using DI water, photoresist was added in between the IDTs of the SH-SAW device having the delay line structure, as previously described. A 5 dB extra attenuation due to the presence of the photoresist was identified. This is another indication that the shear horizontal mode along these orientations has reduced attenuation to allow the deposition of bio or chemical films for liquid sensor applications.

The above described signal amplitude attenuation can be correlated to changes in mass or composition of chemical or biological agents present in a liquid environment. Additionally, similar measurement may be made for frequency shifts, phase shifts or, for delay lines, changes in delay time between the IDT's can be measured for sensors contemplated by the invention. Again, the frequency shift, phase shift and delay time changes can be correlated to liquid properties or constituents present in the liquid. Thus, the inventor believes that the present invention is particularly adapted for use in sensing liquid properties.

Figure 14:
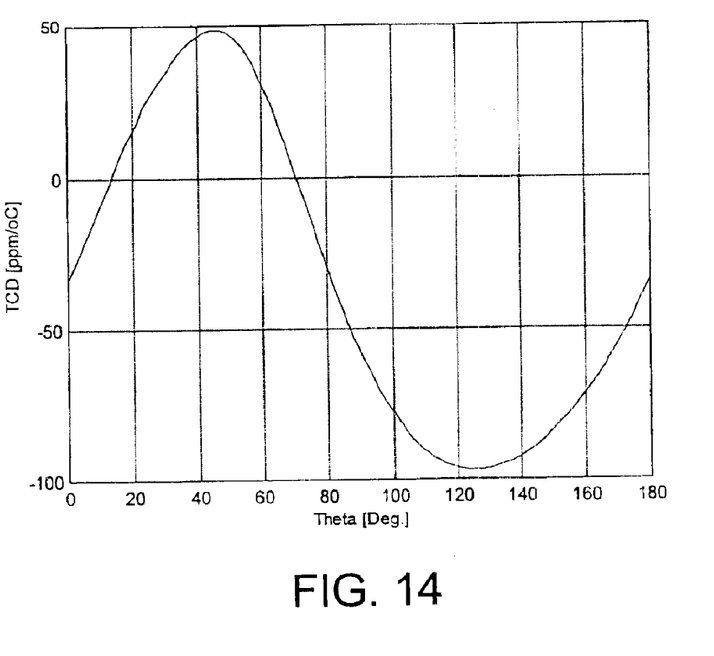
FIG. 14 illustrates a predicted temperature coefficient of delay for a SH-SAW device formed from LGT material in accordance with the invention.
Figure 15:
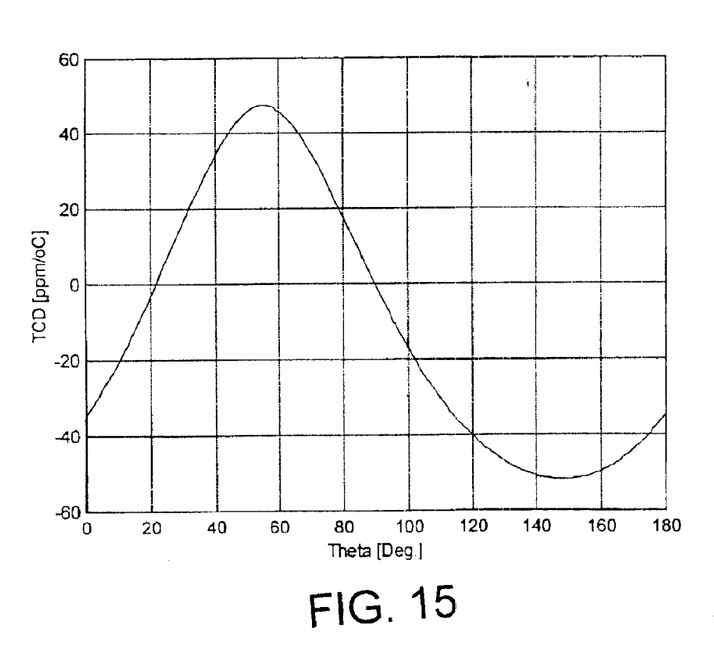
FIG. 15 illustrates a predicted temperature coefficient of delay for a SH-SAW device formed from LGS material in accordance with the invention.
Figure 16:
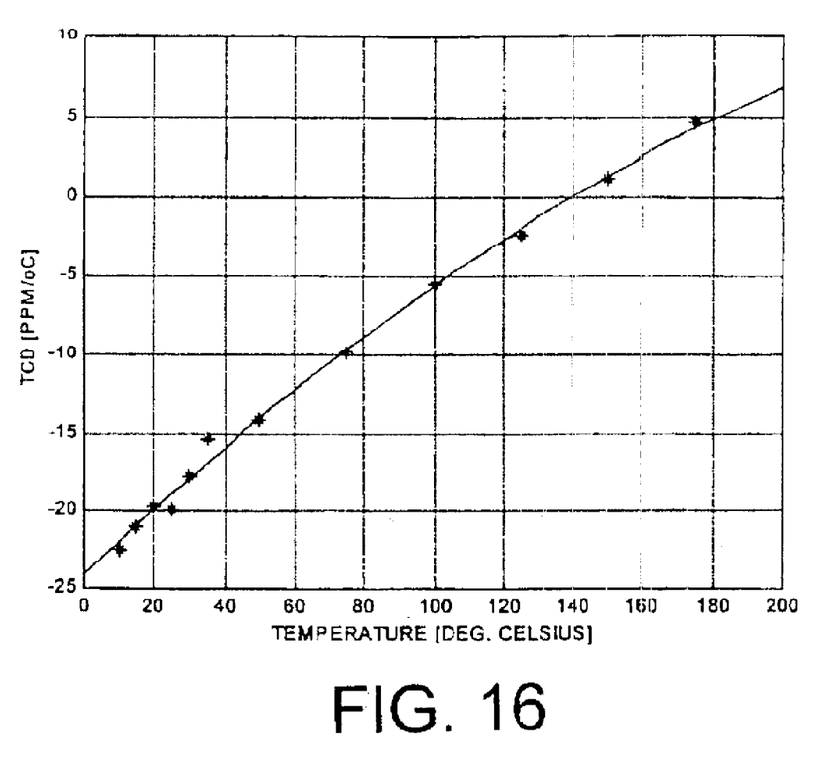
FIG. 16 illustrates a measured temperature coefficient of delay as a function of temperature for a SH-SAW device formed from LGT Euler angles (0°, 13.5°, 90°) in accordance with the invention.

The inventor has performed theoretical calculations and obtained experimental results that indicate the existence of a zero Temperature Coefficient of Delay (TCD) for the propagation directions identified for the present invention. A zero TCD translates into zero or minimal variation of frequency with temperature at a certain temperature and within the vicinity of the certain temperature. This is an important characteristic for electronic devices used in frequency control and sensing. FIGS. 14 and 15 show the predicted TCD for SAW devices formed from LGT and LGS materials, respectively. In FIGS. 14 and 15, the first and third Euler angles are assumed to be 0° and 90°, respectively while the second Euler angle, θ varies from zero to 180 degrees. It is seen that the TDC passes through zero within the range of 0 used in the preferred embodiment of the present invention. FIG. 16 shows measured TCD results as a function of temperature for a SAW device formed from LGT crystals with Euler angles defined as (0°, 13.5°, 90°). In FIG. 16, the experimentally obtained values are indicated by the asterisks while the solid line is a curve that has been fitted to the individual experimentally obtained values.

The SH-SAW wave on the LGX family of crystals along the propagation directions identified for this invention are very appropriate for liquid sensing, to include pharmaceutical, biodefense, medical, bioengineering, chemical, and environmental sensor applications. This is due to the energy guiding very close to the surface of the device, the existence of zero TCD, the high electromechanical coupling for the SH wave, and the high relative permittivity of the LGX family of crystals, which together increase the performance and sensitivity of the sensor. The crystal orientation of the invention was tested in a liquid environment and with photoresist added to the surface and presented the moderate attenuation expected from SH modes on the LGX family of crystals due to the shear horizontal particle polarization and the higher effective permittivity of these materials.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A Surface Acoustic Wave (SAW) Device comprising:
   a substrate formed from langanite (LGN, $La_3Ga_{5.5}Nb_{0.5}O_{14}$) and having a SAW propagation surface, said substrate formed from a crystal having X, Y, and Z crystalline axes; and
   at least one interdigital transducer formed upon said substrate propagation surface, said transducer having electrodes formed upon said propagation surface for launching and detecting surface acoustic waves having a direction of propagation along X''', Y''' and Z''' device axes with the device axis forming Euler angles relative to the corresponding crystalline axes having a range of $-5°<\phi<+5°$, $-5°<\theta<50°$ and $80°<\psi<100°$.

2. The SAW Device according to claim 1 wherein the SAW Device is included in a liquid sensor.

3. The SAW Device according to claim 2 wherein said surface acoustic wave is a quasi-shear horizontal SAW.

4. The SAW Device according to claim 3 wherein the SAW Device detects a change in a parameter of said quasi-shear horizontal SAW, said change in parameter being correlated to a liquid property.

5. The SAW Device according to claim 3 wherein the SAW Device detects a change in a parameter of said quasi-shear horizontal SAW, said change in parameter being correlated to a liquid constituent.

6. The SAW Device according to claim 2 wherein said surface acoustic wave is a pure shear horizontal SAW.

7. The SAW Device according to claim 6 wherein the SAW Device detects a change in a parameter of said pure shear horizontal SAW, said change in parameter being correlated to a liquid property.

8. The SAW Device according to claim 6 wherein the SAW Device detects a change in a parameter of said pure shear horizontal SAW, said change in parameter being correlated to a liquid constituent.

9. The SAW Device according to claim 2 wherein said interdigital transducer is formed from a thin film material deposited upon said substrate propagation surface.

10. The SAW Device according to claim 2 wherein the SAW Device functions as a resonator.

11. The SAW Device according to claim 10 further including at least one reflector grating formed upon said substrate propagation surface adjacent to said interdigital transducer.

12. The SAW Device according to claim 1 including a first transducer and a second interdigital transducer formed upon said substrate propagation surface, said second transducer separated from said first transducer, said first and second transducers co-operating to launch and detect surface acoustic waves having a direction of propagation along X''', Y''' and Z''' device axes whereby the SAW Device functions as a delay line.

13. The SAW Device according to claim 12 wherein the surface acoustic waves propagate in shear horizontal mode of operation.

14. The SAW Device according to claim 13 wherein said surface acoustic waves are pure shear horizontal SAW.

15. The SAW Device according to claim 13 wherein said surface acoustic waves are quasi-shear horizontal SAW.

16. The SAW Device according to claim 13 wherein said substrate is formed from a material selected from one of the group of LGT, LGS, LGN, LGTS and LGZS.

17. The SAW Device according to claim 2 further including at least one film layer deposited over said substrate propagation surface, whereby the sensitivity of the device is enhanced.

18. The SAW Device according to claim 17 wherein said film layer includes a layer of metal on top of an adhesion layer.

19. The SAW Device according to claim 18 wherein said layer of metal is formed from one of the group of Al, Au and Pt and further wherein said adhesion layer includes one of the group of Cr, Ti, and NiCr.

20. A Surface Acoustic Wave (SAW) Device comprising:
    a substrate formed from one of langatate (LGT, $La_3Ga_{5.5}Ta_{0.5}O_{14}$) and langanite (LGN, $La_3Ga_{5.5}Nb_{0.5}O_{14}$) and having a SAW propagation surface, said substrate formed from a crystal having having X, Y, and Z crystalline axes;
    at least one interdigital transducer formed upon said substrate propagation surface for launching surface acoustic waves in a shear horizontal mode; and
    at least one interdigital transducer formed upon said substrate propagation surface for receiving said surface acoustic waves, said transducers having electrodes formed upon said propagation surface for launching and detecting surface acoustic waves having a direction of propagation along X''', Y''' and Z''' device axes with the device axis forming Euler angles relative to the corresponding crystal axes having a range of $-5°<\phi<+5°$, $-5°<\theta<50°$ and $80°\psi<100°$.

21. The SAW Device according to claim 20 wherein said surface acoustic waves are pure shear horizontal SAW.

22. The SAW Device according to claim 20 wherein said surface acoustic waves are quasi-shear horizontal SAW.

23. A Surface Acoustic Wave (SAW) Device comprising:
    a substrate having a substantially planar surface for propagating surface acoustic waves thereon, the substrate formed from a single crystal of langanite (LGN, $La_3Ga_{5.5}Nb_{0.5}O_{14}$), said crystal cut for forming said surface defined by Euler angles having a range of $-5°<\phi<+5°$, $-5°<\theta<50°$ and $80°<\psi<100°$; and at least one interdigital transducer formed upon said substrate propagation surface.

24. A method for forming a Surface Acoustic Wave (SAW) Device comprising the steps of:
   (a) providing a single crystal, langanite (LGN, $La_3Ga_{5.5}Nb_{0.5}O_{14}$);
   (b) orienting the crystal for forming a planar surface, the crystal orientation defined by the Euler angles having a range of $-5°<\phi<+5°$, $-5°<\theta<50°$ and $80°<\psi<100°$:
   (c) forming the planar surface upon the crystal, the planar surface defined by the Euler angles within the ranges of step (b); and
   (d) fabricating at least one interdigital transducer formed upon said substrate propagation surface, said transducer operative with surface acoustic waves propagating in a direction generally along an axis of propagation defined relative to the crystalline axes by the Euler angles ($\phi$, $\theta$, $\psi$).

25. The method according to claim 24 wherein step (c) includes cutting the crystal to form the planar surface defined by the Euler angles within the ranges of step (b).

26. A Surface Acoustic Wave (SAW) device comprising:
   a substrate formed from one of the group of langatate (LGT, $La_3Ga_{5.5}Ta_{0.5}O_{14}$) and langanite (LGN, $La_3Ga_{5.5}Nb_{0.5}O_{14}$) and having a SAW propagation surface, said substrate formed from a crystal having X, Y, and Z crystalline axes; and
   at least one interdigital transducer formed upon said substrate propagation surface, said transducer having electrodes formed upon said propagation surface for launching and detecting shear horizontal surface acoustic waves having a direction of propagation along X''', Y''' and Z''' device axes with the device axis forming Euler angles relative to the corresponding crystalline axes having a range of $-5°<\phi<+5°$, $-5°<\theta<50°$ and $80°<\psi<100°$.

27. The SAW Device according to claim 26 wherein the SAW Device is included in a liquid sensor.

28. The SAW Device according to claim 27 wherein said surface acoustic waves are pure shear horizontal SAW.

29. The SAW Device according to claim 27 wherein said surface acoustic waves are quasi-shear horizontal SAW.

30. A Surface Acoustic Wave (SAW) device comprising:
   a substrate formed from langasite (LGS, $La_3Ga_5SiO_{14}$), and variations of LGS, such as LGTS ($La_3Ga_{5.25}Ta_{0.25}Si_{0.5}O_{14}$) and LGZS ($La_3Ga_5Zr_{0.5}Si_{0.5}O_{14}$), and having a SAW propagation surface, said substrate formed from a crystal having X, Y, and Z crystalline axes; and
   at least one interdigital transducer formed upon said substrate propagation surface, said transducer having electrodes formed upon said propagation surface for launching and detecting shear horizontal surface acoustic waves having a direction of propagation along X''', Y''' and Z''' device axes with the device axis forming Euler angles relative to the corresponding crystalline axes having a range of $-5°<\phi<+5°$, $-5°<\theta<50°$ and $80°<\psi<100°$ whereby the device functions as a liquid sensor.

31. The SAW Device according to claim 30 wherein said surface acoustic waves are pure shear horizontal SAW.

32. The SAW Device according to claim 31 wherein the SAW Device detects a change in a parameter of said pure shear horizontal SAW, said change in parameter being correlated to a liquid property.

33. The SAW Device according to claim 32 wherein the SAW Device detects a change in a parameter of said pure shear horizontal SAW, said change in parameter being correlated to a liquid constituent.

34. The SAW Device according to claim 30 wherein said surface acoustic waves are quasi-shear horizontal SAW.

35. The SAW Device according to claim 34 wherein the SAW Device detects a change in a parameter of said quasi-shear horizontal SAW, said change in parameter being correlated to a liquid property.

36. The SAW Device according to claim 34 wherein the SAW Device detects a change in a parameter of said quasi-shear horizontal SAW, said change in parameter being correlated to a liquid constituent.

* * * * *